United States Patent [19]

Corbett

[11] Patent Number: 4,537,198

[45] Date of Patent: Aug. 27, 1985

[54] ELECTRODE CAP

[76] Inventor: Sue Corbett, 901 Harvard Pl., Woodland, Calif. 95695

[21] Appl. No.: 491,238

[22] Filed: May 3, 1983

[51] Int. Cl.³ .............................................. A61B 5/04
[52] U.S. Cl. .................................... 128/639; 128/644
[58] Field of Search ........................ 128/644, 639–641, 128/803, 802, 731, 732

[56] References Cited

U.S. PATENT DOCUMENTS

| | | | |
|---|---|---|---|
| 3,534,727 | 10/1970 | Roman | 128/644 |
| 3,669,110 | 6/1972 | Frost, Jr. | 128/639 |
| 3,735,753 | 5/1973 | Pisarski | 128/644 |
| 3,998,213 | 12/1976 | Price | 128/644 |
| 4,026,278 | 5/1977 | Ricketts et al. | 128/644 |
| 4,072,145 | 2/1978 | Silva | 128/644 |
| 4,085,739 | 4/1978 | Sams | 128/644 |
| 4,323,076 | 4/1982 | Sams | 128/644 |

FOREIGN PATENT DOCUMENTS 676273  7/1979  U.S.S.R. ............................. 128/644

OTHER PUBLICATIONS

Hanley et al, "Electrode Systems . . . ," Biomed. Electrode Tech., Academic Press, pp. 283–313, 1974.

*Primary Examiner*—Lee S. Cohen
*Attorney, Agent, or Firm*—William R. Laney

[57] ABSTRACT

An electrode cap for use in encephalographic analysis which includes a flexible head cover having a plurality of spaced electrode anchor tabs disposed on the inner side thereof. Flexible electrode lead wires extend through the head cover and are attached to electrodes inside the cover. Each electrode is mounted in an independently positionable engaging tab which is adapted to be selectively positioned by finely adjustable contact engagement with one of the anchor tabs at a preselected locus. The head cover is preferably of multi-panel construction, including a crown flap which can be folded between opened and closed positions, thereby facilitating ready access to the interior of the head cover and ease of replacement or repair of one or more of the electrodes and the respective lead. An electrode board adapter is provided for connecting the electrodes to the E.E.G. amplifier and readout instrument.

24 Claims, 16 Drawing Figures

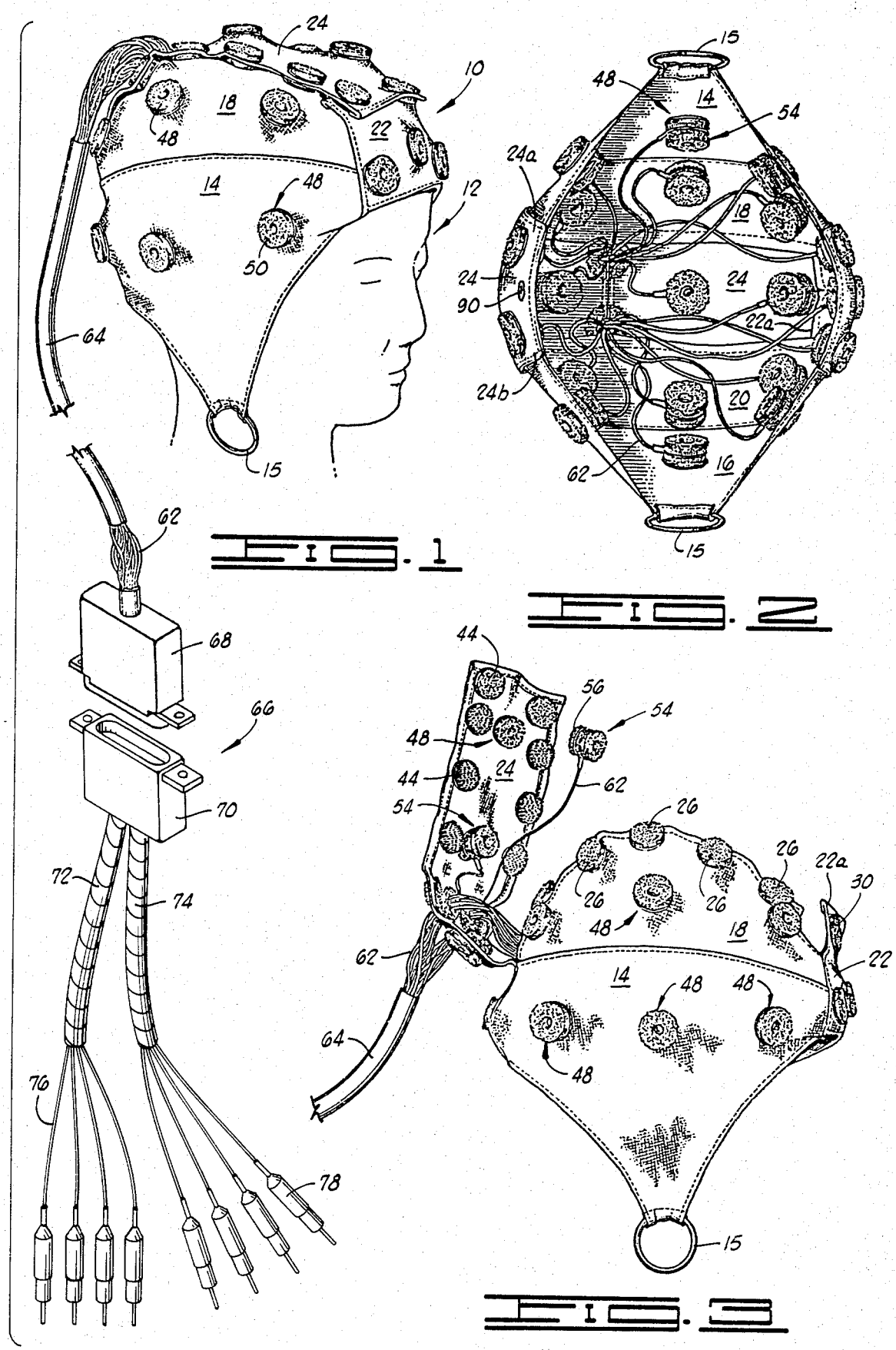

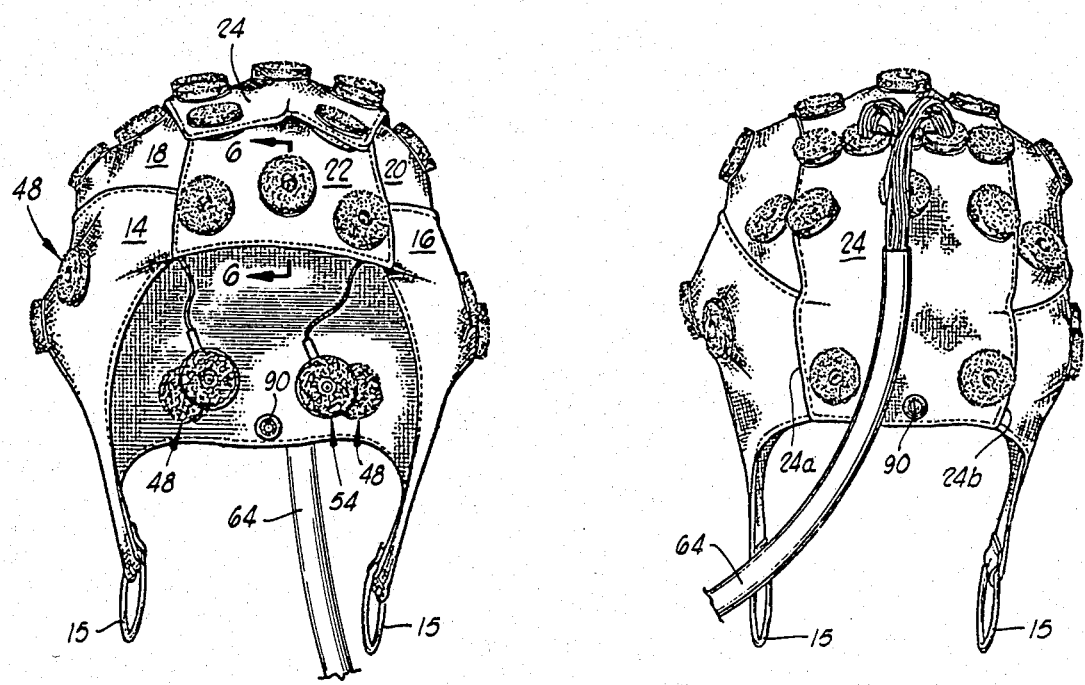
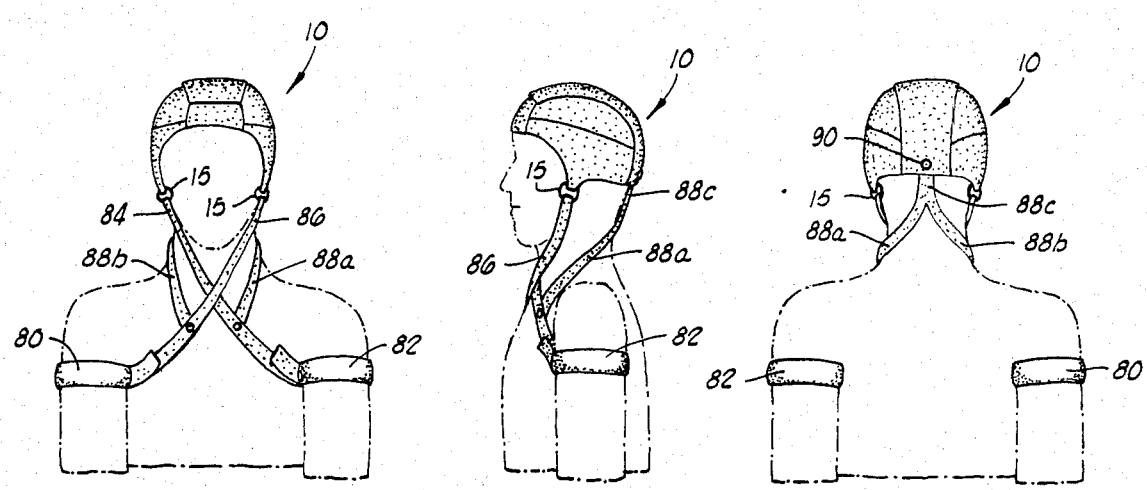

U.S. Patent  Aug. 27, 1985  Sheet 3 of 3  4,537,198
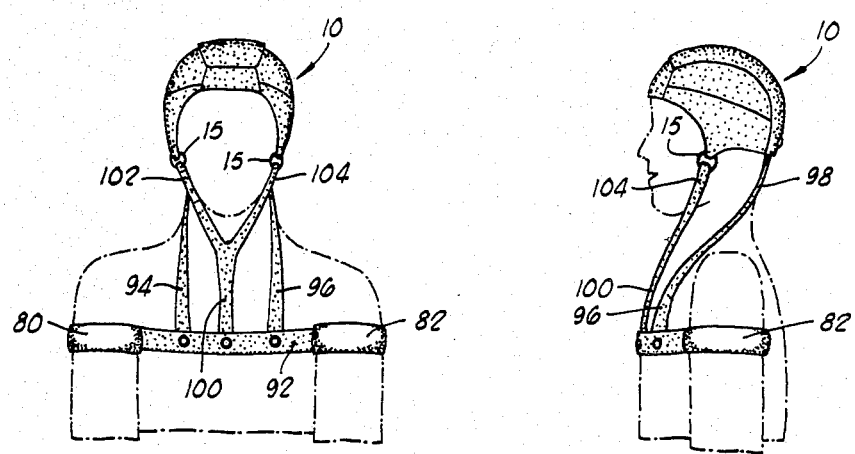
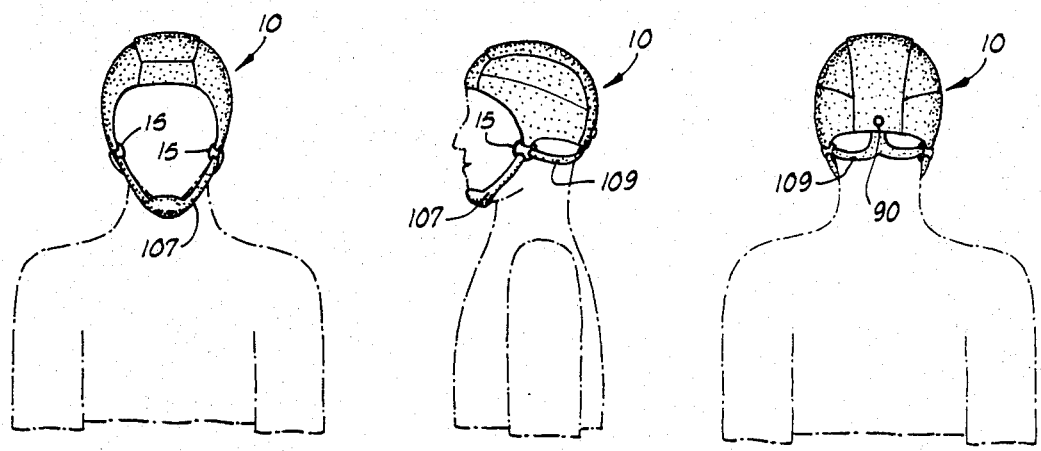
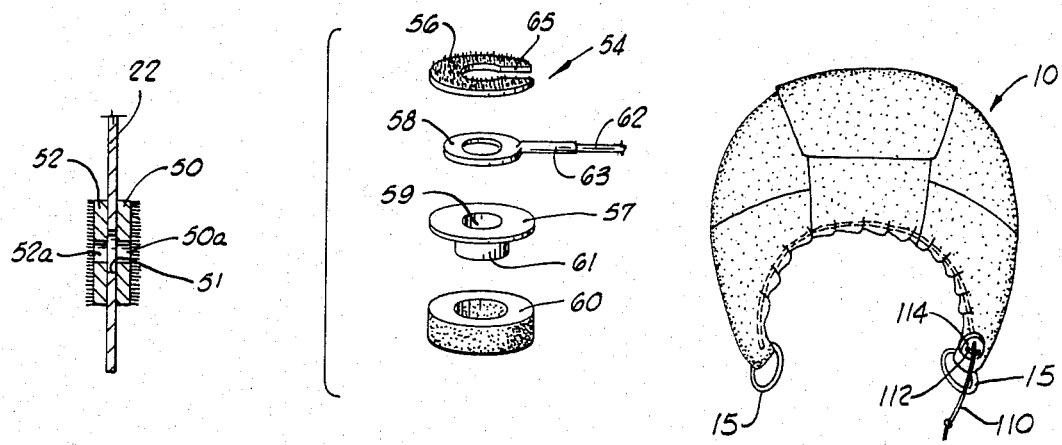

ELECTRODE CAP

FIELD OF THE INVENTION

This invention relates to electrode caps of the type which are employed in encephalographic analysis, and which include a head cover upon which is mounted, or which is adapted to have mounted thereon, a plurality of brain wave responsive electrodes.

BACKGROUND OF THE INVENTION

Brief Description of the Prior Art

An electroencephalograph is an instrument for recording the electric activity of the brain by means of electrodes attached to, or in electrical contact with, the surface of the scalp. The instrument is used in the diagnosis of epilepsy, trauma, tumors and the degenerations and malfunctions of the brain.

A number of types of electrode caps for use in encephalographic analyses have been heretofore proposed, and many are described in United States patents. These devices have also been the subject of many articles and papers appearing in the technical literature.

As described in the E.E.G. Handbook, Second Edition, authored by Alice Craib and Margaret Perry, copyright Beckman Instruments, Inc., 1973 and 1975, the authors describe some of the problems which have characterized efforts to optimize encephalographic electrode caps. Craib et al indicate that it has been difficult to provide a cap construction which is economically feasible, yet electrogpraphically reliable. The authors describe a cap developed for use by astronauts in space exploration. A disadvantage which has characterized these caps is indicated to be the fact that the electrode positions are fixed, and are not individually adjustable for the requirements peculiar to each individual electrographic analysis and patient. Moreover, the construction is such that it is not possible to replace individual electrodes if they become defective or damaged. Rather, the entire cap must replaced.

Another art-recognized desideratum in electrode cap design is the elimination of artifacts due to positioning of the electrodes too close to the skull, or resulting from movement of the head of the patient relative to the cap and the electrodes carried thereby. It is also of paramount importance to avoid electrical shock and the employment of combustible or chemically reactive interface pastes is to be avoided.

In some of the proposed electrode caps heretofore patented and/or in use, two part electrode elements are provided which snap together to provide electrode exposure in the inner side of the cap, and an electrical connection to a detachable lead on the outer side of the cap. One such construction is described and illustrated in Sams U.S. Pat. No. 4,323,076.

Many of the caps previously proposed are made of an elastic material, or of a group of elastic straps which collectively hold and position the electrodes adjacent the scalp of the patient. When placed in position on the head of the patient such head gear is alleged to reduce the possibility of shifting or movement of the electrodes, or loss of electrical contact with the patient during taking of the electroencephalogram.

Generally, placement of the electrodes relative to the skull follows a standardized and systematic arrangement which is conventional in the art. For the most part, the types of electrode caps which have been proposed, depend upon rather precise measurement of electrode position on the fabric of the cap during its construction, and proper positioning of the electrodes is thus dependent upon the accuracy of this original measurement and construction.

Various methods have been proposed for retaining the cap on the patient's head during the taking of the electroencephalogram. Chin straps which pass from opposite sides of the cap under the chip of the patient are sometimes utilized. In other arrangements, such as that shown and decribed in U.S. Pat. No. 4,085,739, a chest harness is utilized so that, should the patient's chin move during the analysis, spurious signals are not developed as a result of such movement, and the cap is maintained in a relatively stable and unshifting location on the patient's head.

In an article entitled "Electrode Systems for Recording the E.E.G. in Active Subjects," Hanley, Hahn and Adey, describe an expandable Lycra electride helmet which carries grommets sewn into the helmet at spaced locations. Internal sponge electrodes snap into these grommets, and an electrolyte gel is used to soak the sponge electrode tips for establishing a good electrical path to the scalp. The Hanley et al article appears in BioMedical Electrode Technology, Academic Press, 1974.

In an article "A Method for Locating Scalp Electrodes and Spherical Coordinates," Ary, Darcey and Fender, IEEE Transactions of BioMedical Engineering, Vol. Eme-28, No. 12, December, 1981, an electrode cap is described in which the electrodes are cylindrical elements which are plugged into rubber bumper grommets located at spaced locations around the cap. These electrodes are fixed in their positions once the cap is assembled, and cannot be spaced at any selected spacing other than those dictated by the location of the rubber bumper grommets into which they are received. An elastic strap is used to hold the helmet or cap on the head of the patient.

Rolston U.S. Pat. No. 3,490,439, describes an electrode cap made up of a plurality of interconnected straps which carry a series of spaced electrodes. These electrodes are detachable from the straps, so that should one of the electrodes become defective, it can be individually replaced.

In U.S. Pat. No. 3,669,110 to Lowe et al, a disposable sponge electrode is described which can be suitably mounted in an electrode cap, and which incorporates a paste-like electrolyte material in the sponge to establish good ohmic contact with the scalp of the patient.

In U.S. Pat. No. 3,998,213, a self-adjustable holder for automatically positioning encephalographic electrodes is disclosed. The holder consists of a group of straps which are arrayed to form a head-shaped cap which is elastically expandable, and thus is self-adjustable to snugly fit the patient's head. A plurality of electrode positioning elements are located on the straps at various points, and each is adapted to hold an electrode in contact with the head at a precise position. The electrode positioning elements are made of a rigid material, and have an opening therethrough for the insertion of an associated electrode. The electrodes are made of a conductive sponge material of a type conventionally employed, and are impregnated with a conductive cream or gel of electrolyte material.

In Ricketts U.S. Pat. No. 4,026,278, a belt is provided for surrounding the body for use in electrocardiogram procedures. On the inner surface of this belt, Velcro loop fabric is attached. A series of electrodes are each provided on one side with Velcro hook fabric, and this permits the electrodes to be removably secured to the inner side of the belt at any selected locations therealong. In a different embodiment of the invention, the electrodes may be snap-engaged with cooperating snap elements carried on the belt at various locations therealong. The Velcro construction of the inner side of the belt enables the electrodes, when they carry Velcro hook fabric, to be quickly removed from the belt simply by pulling them off, and to then be repositioned by pressing them back onto the belt at the newly desired locations. The number of electrodes employed can be varied.

A generally similar attachment system is described U.S. Pat. No. 4,072,145 to Silva. Here a head band assembly of electrodes for sensing signals of brain wave frequency is disclosed. The assembly includes a head band and is constructed of self-adherent Velcro material. The electrode subassemblies include superimposed or sandwiched Velcro pads with the innermost pad (closest to the scalp) being silver plated to afford conductivity. The Velcro outer pad of each electrode subassembly can be adhered at any selected location along the band, which is placed around the patent's head. The several electrode assemblies can thus be shifted along the band as desired to adjust their location relative to the cranium.

In U.S. Pat. No. 4,033,334, a replaceable electrode is disclosed which is constructed to include a plastic housing containing a sponge body which is filled with conductive electrolyte gel. The base of the housing is formed of a conductive plastic material and has at its center, a snap-engaging element. This element cooperates with a co-acting snap element located on a washable electrode cap. The electrode may be easily replaced at any time or following each use. As in many other types of prior art electrode caps, the correct positioning of the electrodes against the scalp is accomplished by precision fitting of the cap.

The described devices for positioning various types of electrodes in electrical contact with the scalp of a person undergoing an electroencephalographic analysis still lack flexibility and universality in the capability they afford for selectively and precisely adjusting the postion of numerous electrodes relative to the cranium of the patient. Moreover, the time required to achieve the necessary electrode positioning preparatory to commencing to record the brain wave signals is still unacceptably lengthy.

GENERAL DESCRIPTION OF THE PRESENT INVENTION

The present invention provides an easily used electrode cap which can be very quickly placed on the head of a patient, is self-adjusting to fit the particular head size of virtually any patient, and which, by reason of the novel method of electrode positioning and attachment, facilitates the exact location of a number of electrodes at precisely selected locations on the interior of the cap and in relation to the patient's head. The cap can be economically constructed, is light in weight, and permits any individual one of the electrodes to be replaced at any time that it may become defective.

Broadly described, the electrode cap of the invention includes a flexible fabric head cover having a plurality of spaced electrode anchor tabs disposed on the inner side thereof. A plurality of electrode lead wires extends through the head cover and each lead is attached to an electrode located interiorly of the cover. Each electrode is mounted in an independently positionable engaging tab which includes a sponge element at one side thereof and an engaging element at the opposite side thereof. Each engaging element is adapted to be selectively and finely adjustably engaged to the inside of the head cover by contact with a pre-selected locus on one of the anchor tabs. The head cover is preferably a multi-panel helmet including a crown flap which can be folded between an opened and a closed position. In the closed position the crown flap is quick detachably secured to the remainder of the multi-panel helmet. The detachable, foldable character of the crown flap facilitates ready access to the interior of the head cover, and the electrodes can be easily replaced or repaired if required.

The flexible fabric head cover is retained on the head of the patient in any one of several ways, including by means of a chin strap or an across-the-chest harness.

The invention further contemplates, for use in conjunction with the electrode cap, an electrode board adapter assembly by which the electrodes are connected to the E.E.G. amplifier and readout instrument. The electrode board adapter assembly includes a male cable connector block to which the leads from the electrodes are connected. The male cable connector block is connected to the E.E.G. instrument by means of a female cable connector connectible to the male cable connector. Electrode wires extend from the female connector to individual electrode jacks carried at the distal end of each of the electrode wires. The jacks interface to the electrode board of the E.E.G. instrument.

An object attained by the electrode cap of the invention is the ability to accurately position and locate the electrodes in an accurate International 10-20 System of electrode placement on each individual patient, using the same basic cap structure and despite variations in the shape and size of the patient's skull, through selective fine adjustment in the location and placement of a selected number of electrodes inside the cap.

Another object of my invention is to enable E.E.G. technologists to avoid placing electrodes over skull defects, such as scars, burr holes, suture lines and the like, thereby avoiding the development of artifacts and undesired spurious electrical potentials in the generation of the E.E.G. data.

A further object attained by my invention is facilitation of sampling of an exact cortical area by exact predetermined placement of the E.E.G. recording electrodes so that localized brain disfunctions can be accurately and quickly diagnosed.

A further object of my invention is to provide, on the interior of an electroencephalogram electrode cap, a plurality of comfortable, non-invasive electrode elements which minimize irritation to the scalp of the patient.

A futher object of the invention is to provide an electrode cap in which individual electrodes can be quickly and easily replaced when any such electrode becomes defective or malfunctions.

Additional objects and advantages of the invention will become apparent as the following detailed description of the invention is read in conjunction with the accompanying drawings which illustrate several preferred embodiments of my invention.

GENERAL DESCRIPTION OF THE DRAWINGS

FIG. 1 is a side elevation view of the electrode cap and electrode board adapter assembly of the invention, with the cap shown mounted on the head of a patient.

FIG. 2 is a bottom plan view of the electrode cap of the invention illustrating the manner in which electrodes located on the interior of the cap are positioned by selective attachment to a plurality of electrode anchor tabs carried on the interior of the cap.

FIG. 3 is a side elevation view of the electrode cap of the invention with the cranial flap lifted to provide access to the interior of the cap and to the electrodes.

FIG. 4 is a front elevation view of the electrode cap.

FIG. 5 is a rear elevation view of the cap as it appears when viewed from the rear.

FIG. 6 is a sectional view taken along line 6—6 of FIG. 2.

FIG. 7 is an exploded view of one of the pickup electrodes used in the invention.

FIG. 8 is a front elevation view of a patient, shown in dashed lines, wearing the electrode cap of the invention, and illustrating a harness which can be used to retain the electrode cap in a stable position on the patient's head during the development of the electroencephalogram.

FIG. 9 is a side elevation view of the cap, harness and patient shown in FIG. 8.

FIG. 10 is a rear elevation view of the cap, patient and harness shown in FIG. 8.

FIG. 11 is a front elevation view of a different cap stabilizing harness used in combination with the electrode cap of the invention.

FIG. 12 is a side elevation view of the cap and harness shown in FIG. 11.

FIG. 13 is a front elevation view of yet another embodiment of a cap retainer structure.

FIG. 14 is a side elevation view of the cap and cap retainer structure shown in FIG. 13.

FIG. 15 is a rear elevation view of the cap and cap retainer structure shown in FIG. 13.

FIG. 16 is a front elevation view of a modified embodiment of the electrode cap of the invention.

DETAILED DESCRIPTION OF THE PREFERRED EMBODIMENTS OF THE INVENTION

Referring initially to FIG. 1 of the drawings, the electrode cap of the invention is designated generally by reference numeral 10, and is illustrated in position on the head 12 of a patient. The electrode cap 10 includes a head cover or helmet made up of multiple interconnected panels. Thus, the head cover includes right and left ear flap panels 14 and 16. The ear flaps panels 14 and 16 carry rigid rings 15 at their lower ends, and are respectively connected to a right upper panel 18 and to a left upper panel 20. The right and left ear panels 14 and 16, as well as the right and left upper panels 18 and 20, are joined along their forward edges to a forehead panel 22. The described panels are interconnected in any suitable way, but in a preferred embodiment of the invention are stitched along the lines illustrated in the drawings to interconnect the several panels at their adjacent edges. The material of which the helmet or head covering is made is of a wide or coarse weave so that the patient's head can be seen through the helmet from the outer side thereof.

The head cover further includes a crown panel 24 which has a rear portion having opposed edges 24a and 24b which are stitched to the rear inner edges of the right and left ear panels 14 and 16 as best illustrated in FIG. 5. The crown panel 24 is generally rectangular in configuration and is adapted to extend across and cover the space between the inner edges of the right and left upper panels 18 and 20 as illustrated in FIGS. 1, 4 and 5. Moreover, the crown panel 24 is also of a length such that it extends to the upper transverse edge 22a of the forehead panel 22.

For the purpose of enabling the crown panel 24 to be secured in a closed position in which it overlaps and is joined to the right and left upper panels 18 and 20, and to the upper transverse edge of the forehead panel 22, a plurality of spaced Velcro attachment tabs 26 are secured to the inner edges of each of the upper panels 18 and 20 as illustrated in FIG. 3, and in like manner, a plurality of spaced Velcro attachment tabs 30 are secured along the transverse upper edge of the forehead panel 22. Mating Velcro attachment tabs 44 are secured along the lateral edges and forward edge of the crown panel 24 as illustrated in FIG. 2, and in conventional fashion, engage the Velcro tabs 26 and 30 on the upper panels 18 and 20 and on the forehead panel 22 when the crown flap is placed in its closed position as illustrated in FIGS. 1, 2, 4 and 5.

At various pre-selected locations around the head cover of the electrode cap 10, a plurality of spaced electrode anchoring tabs 48 are located. Each of the spaced electrode anchoring tabs 48 includes an annular outer disc 50 and an annular inner disc 52 which are glued or otherwise suitably secured to the panels of the electrode cap. Each of the annular discs defines a central aperture or opening 50a and 52a therethrough. The outer disc 50 and inner disc 52 can be secured to the fabric of the head covering in any suitable fashion, such as by gluing, and are positioned over an opening 51 through the head cover so that openings or apertures 50a and 52a, formed through the two discs, are aligned with the opening through the head cover or helmet, and are aligned with each other as shown in FIG. 6. This arrangement facilitates the injection of a semi-liquid or paste-like electrolyte through the openings 50a and 52a so that the electrolyte can pass to a pickup electrode secured to the inner disc 52 of the anchoring tab 48 on the inner side of the cap in a manner hereinafter described. The inner disc 52 is preferably constructed of a Velcro material, and the outer disc 50 can be similarly constructed.

The number and particular geometric array of the electrode anchoring tabs 48 which are provided on the head cover or helmet can be varied to suit particular diagnostic or analytical desiderata, as will be hereinafter explained. The specific anchoring tab array used in the construction of the electrode cap of the present invention is less critical to the final positioning of the electrodes than has been characteristic of other means previously provided on prior art electrode caps for securing the electrodes thereto in order to precisely orient the electrodes in relation to the cranium of the patient.

A plurality of internal pickup electrodes are provided and are designated generally by reference numeral 54. Each of the internal electrodes includes a disc-shaped Velcro anchoring element 56 which is secured to an annular synthetic resin mounting plate 57. The mounting plate 57 has a hole 59 through the center thereof and through a tubular boss 61 which projects concentrically from one side of the mounting plate.

An annular metallic contact 58 is mounted between the mounting plate 57 and the Velcro disc 56, and carries a lead attachment neck 63 which projects through a radial slot 65 in the Velcro disc. A foamed closed cell synthetic resin annular pad 60 is secured by adhesive or any other suitable means to the mounting plate 57 and surrounds and projects beyond the boss 61 carried thereon. It will be noted in referring to FIG. 7 that the openings through the Velcro disc 56, the annular metallic contact 58, and the synthetic resin mounting plate 57 are aligned. It will also be noted that the bore through the boss 61 is of larger diameter than the central opening in the annular metallic contact 58. This arrangement permits a semi-liquid or paste-like electrolyte to pass through the aligned central openings to a location where the electrolyte is in contact with the scalp of the patient and also with the contact 58 as will be hereinafter explained in greater detail.

Secured to each of the annular metallic contacts 58 is one end of a lead wire 62. The multiple lead wires from the internal pickup electrodes 54 pass, in a closely adjacent relationship, through two openings formed in the crown flap 24 at a location relatively near to the rear portion of the crown flap which is joined to the side panels 14 and 16. After passing through these openings in the crown flap 24, the lead wires 62 are sheathed in a protective insulating tubular element 64 as shown in FIGS. 1 and 3.

An electrode board adapter assembly, designated generally by reference numeral 66 is utilized in conjunction with the electrode cap 10. The electrode board adapter assembly 66 includes a male cable connector block 68 which interfaces with, and connects to a female cable connector 70. A pair of electrode lead tubular harnesses 72 and 74 extend from the female cable connector 70 and encase a plurality of leads 76. Each of the leads 76 is connected at its free end to an electrode jack 78. The electrode jacks 78 are adapted to be plugged into the electrode board of the E.E.G. instrument when the electrode cap is in use.

Several types of harnesses or mounting assemblies by which the electrode cap 10 is retained on the head of the patient during use are illustrated in FIGS. 8–15. One arrangement, illustrated in FIG. 8, includes a pair of arm bands 80 and 82 which, in use, encircle the arms of the patient and carry means suitable for connecting the arm bands to a pair of cross straps 84 and 86. The cross straps 84 and 86 are connected at one end to the rings 15 carried at the lower sides of the ear flap panels 14 and 16. The cross straps 84 and 86 are connected at their opposite ends to the arm bands 80 and 82. In the embodiment of the invention illustrated in FIGS. 8–10, the cross straps are shown secured to the arm bands 80 and 82 by means of cooperating Velcro tabs carried thereon.

To further assure the stability of the electrode cap 10 on the head of the patient during the taking of an encephalogram, a bifurcated rear anchor strap, which includes a pair of branch straps 88a and 88b and a main trunk 88c which is snapped to a snap element 90 carried at the lower rear edge of the helmet is provided. The pair of branch straps 88a and 88b which extend around the neck of the patient and across the shoulders, have their ends snap engaged with the cross straps 84 and 86, as shown in FIGS. 8 and 9.

Another type of head cover-retaining harness assembly is illustrated in FIGS. 11 and 12. Here the arm bands 80 and 82 illustrated in FIGS. 8–10, and previously described, are interconnected by a horizontally extending, transverse chest strap 92. Snap engaged with the chest strap 92 are a pair of lateral retainer straps 94 and 96 which extend around the neck of the patient and to a single trunk 98 similar to that shown in FIG. 10. A bifurcated central strap element has a lower main trunk 100 which is snap engaged with the cross strap 92, and a pair of branch straps 102 and 104 which are connected to the rings 15 carried on the head cover ear flap panels 14 and 16.

A simpler chin strap-type securement for the electrode cap is illustrated in FIGS. 13–15. In this arrangement, a chin strap 107 is utilized in conjunction with a bifurcated neck strap 108.

In FIG. 16 of the drawings, a modified embodiment of the electrode cap of the invention is illustrated. In the modified embodiment, provision is made for adjustment of the size of the cap to enable it to more snugly fit relatively smaller or larger heads. The modified embodiment of the electrode cap illustrated in FIG. 16 includes an elastic band 110 which is secured at spaced intervals to the fabric of the cap along the forward lower edge of the forehead panel 22, and the forward edges of the ear flap panels 14 and 16. This results in a puckering or gathering of the fabric head cover or helmet at the forward side thereof to reduce the effective size of the helmet. The elastic band 110 can be expanded, however, and the gathers in the fabric of the head cover can be opened out so as to enlarge the size of the helmet. For this purpose, the elastic band 110 is extended through a hole 112 formed in a button 114 attached to the lower end of the right ear flap panel 16, and in this way, the extent to which a fabric is gathered can be adjusted by pulling the elastic band further through the hole in the button 114, and securing it at that location, or by releasing some of the tension in the elastic band to form the gathers, and thus reduce the size of the head cover or helmet.

OPERATION

In the utilization and operation of the electrode cap 10 of the invention, an appropriate number of electrodes 54 are positioned for location inside the head cover by extension of the electrical lead wires 62 from such electrodes through openings formed near the rear portion of the crown flap 24, as illustrated in FIG. 3. When this has been accomplished, the selected number of pickup electrodes 54 can then be positioned precisely at the desired location in relation to the scalp or cranium of the patient to afford sensitive and accurate monitoring of brain wave potentials at certain critical and selected locations.

The electrode cap 10 of the invention is especially well suited for such precise positioning, since the electrodes 54 can be finely adjusted in their positions inside the head covering. Such fine positioning is accomplished by adhering the disc-shaped Velcro anchoring elements 56, forming a part of each of the pickup electrodes, to the adherent annular inner disc 52 of the several electrode tabs 48. The electrode anchoring tabs 48 to which the pickup electrodes are engaged will be those which are closest in their location to the points on the cranium that the technician determines to be locations where an electrically conductive path is to be established by contact of the pickup electrode and a suitable electrolyte with the scalp of the patient. The specific construction of the anchoring tabs 48 and the pickup electrodes 54 permit the pickup electrodes to be either centered directly over and in line with, certain ones of the anchoring tabs, as shown in FIG. 2, or offset with respect to the central axis of one or more of the electrode anchoring tabs as shown in FIG. 4. This capability of offsetting the pickup electrodes 54 relative to the anchoring tabs 48 permits a wide range of slightly different locations to be realized in the placement of each one of the pickup electrodes and thus greater precision in arranging these electrodes for contact with critical areas on the scalp can thus be achieved.

When a pickup electrode 54 is directly centered over, and in precise registry with, one of the anchoring tabs 48, then the electrically conductive electrolyte paste or semi-liquid can be injected through the aligned openings 50a and 52a in the respective anchoring tab 48, through the central opening in the Velcro anchoring element 56 of the electrode, through the hole in the center of the metallic contact 58 and through the foamed synthetic resin annular pad constituting the innermost part of each of the pickup electrodes. This annular pad 60 cushions the contact of the pickup electrode with the scalp of the patient. It also distributes the electrolyte into direct contact with the scalp of the patient without saturating the closed cell pad and thus eliminating messy and wasteful spreading of excessive electrolyte over unnecessary areas of the scalp. Assurance is gained that a good signal will be received by the metallic contact 58 and conducted via the electrode board adapter assembly 66 to the E.E.G. instrument for recordation.

In those instances where a pickup electrode 54 is axially offset from the electrode anchoring tab 48 to which it is adhered, the wide mesh character of the fabric of which the head cover or helmet is constructed affords sufficient see-through visibility that the technician can visually discern the precise location of the offset pickup electrode, including its open central portion. In these circumstances, a syringe, hypodermic needle or pipette tip can be inserted through the fabric of the helmet and into the central opening in the disc-shaped Velcro anchoring element 56. The electrolyte ejected from the syringe needle, or pipette then passes through the aligned central openings in the anchoring element 56, the annular metallic contact 58 and the foamed synthetic resin pad at the inner side of the off-set electrode.

When the several pickup electrodes 54 have thus been selectively positioned, and electrolyte placed on the inner side of the annular pads 60 where they contact the scalp, the E.E.G. instrument is energized and the brain wave signals are recorded.

As is well understood in the art, the exact cortical areas which are monitored in clinical electroencephalogram analyses are based on three skull benchmarks, namely, the nasion, inion and pre-auricular points. On the basis of these benchmarks, an electrode placement system has been devised termed The International 10/20 System. The utilization of this system enables relatively accurate placement of the cutaneous pickup electrodes over certain known, anatomical sites. Such placement is, of necessity, based upon the average human skull, however, and small variations from the mean location of the nasion, inion and pre-auricular points will occur from individual to individual. The construction of the electrode anchoring tabs 48 and the pickup electrodes 54 of the present invention provides adequate flexibility and selectivity to permit precise conformity to the correct anatomical areas of the skull of substantially any individual tested, despite such individual variations of the location of the nasion, inion and pre-auricular points.

Moreover, in some instances, certain skull defects such as scars, burr holes, and suture lines will occur in the skull of a particular individual. It is desirable to avoid placement of the pickup electrodes 54 directly over these defects in order to avoid the development of artifacts and undesired electrical potentials. The ability to slightly shift or alter the position of any one or more of the pickup electrodes 54 in the manner hereinbefore described permits placement over such skull defects to be avoided.

In addition, sampling from an exact cortical area by precise placement of the pickup electrodes is imperative in diagnosing some localized brain dysfunctions, such as some types of seizure disorders (epilepsy). Some anticonvulsant medications are specific for the treatment and control of epileptiform activity in certain areas of the brain. For these reasons, the proper treatment of the neurological problem can often depend upon the accuracy of the localization (through accurate placement of the pickup electrodes) of the complete area of electrical dysfunction in the brain.

The electrode lead wires are connected in the electrode board adapter so that the leads can be replaced without soldering simply by manual disconnection and reconnection of contact attachments. This quick mode of replacement of both the leads and electrodes is true not only of the leads directly from each one of the pickup electrodes 54, but also of the leads 76 which extend from the female cable connector 70 to the jacks 78.

The several types of harness assemblies used for assuring stability of the electrode cap 10 on the patient, and illustrated in FIGS. 8–15, can be selectively employed, depending on the ability of the patient to maintain the head relatively immobile and steady over an extended period of time, and also upon the individual patient's preference and comfort considerations.

Although certain preferred embodiments of the invention have been herein described in order to enable one having skill in the art to practice the invention, and to follow the underlying principles, it will be understood that various changes and innovations in the described and illustrated structures can be effected and carried out without departure from these basic principles. Changes and innovations of this type are therefore deemed to be circumscribed by the spirit and scope of the invention, except as the same may be necessarily limited by the appended claims, or reasonable equivalents thereof.

What is claimed is:

1. An electrode cap comprising:
   a flexible helmet including:
   a pair of opposed side portions adapted for positioning at particular locations on the head of a patient;
   a flexible crown flap connected to said side portions; and
   means for detachably engaging the crown flap to said opposed side portions to position the helmet upon the head of an individual;
   a plurality of spaced electrode anchoring tabs positioned at least partially inside the helmet and arrayed over a major portion of the interior thereof, each of said tabs including attaching means adapted for removably attaching a pickup electrode to the respective one of said tabs;

a plurality of brain wave pickup electrodes movably located within the interior of the helmet, and each including means to selectively engage said attaching means of any selected one of said anchoring tabs at variable positions thereon; and means for electrically connecting the electrodes to a recording means.

2. An electrode cap as defined in claim 1 wherein each of said side portions comprises:

an ear flap panel; and an upper panel connected to the upper edge of the ear flap panel and adapted to engage said crown flap.

3. An electrode cap as defined in claim 2 and further characterized as including a metallic ring carried on each of said ear flap panels at the lower end thereof.

4. An electrode cap as defined in claim 2 and further characterized as including:

a chin strap having opposite ends connected to said ear flap panels and adapted to pass under and engage the chin of a patient wearing the helmet; and a bifurcated rear strap element including a trunk strap connected to the rear portion of said crown flap; and branch straps each having one end connected to said trunk strap and having second ends connected to said chin strap.

5. An electrode cap as defined in claim 1 wherein said means for detachably engaging the crown flap to said opposed side portions comprises:

a forehead panel interconnecting said side protions; and means for detachably engaging said forehead panel with said crown flap.

6. An electrode cap as defined in claim 5 and further characterized as including means extending across said forehead panel and said side portions for selectively altering the size of said helmet.

7. An electrode cap as defined in claim 6 wherein said means for selectively altering the size of said helmet comprises an elastic band secured to said forehead panel and side portions at spaced locations to gather the material of the helmet when the elastic band is relaxed.

8. An electrode cap as defined in claim 1 wherein said means for electrically connecting the electrodes to a recording means includes lead wires extending from said pickup electrodes through openings in said crown flap.

9. An electrode cap as defined in claim 1 wherein said helmet has openings therethrough and wherein each of said anchoring tabs comprises:

an annular outer disc having a central opening formed through the center thereof; and an annular inner disc having a central opening aligned with the central opening in said outer disc, said outer disc being secured to the outer side of said helmet over one of the openings therethrough, and said inner disc being secured to the inner side of said helmet to place the openings in the discs in communication through the opening through the helmet.

10. An electrode cap as defined in claim 1 and further characterized as including means for stabilizing the helmet on the head of a patient during an encephalographic analysis comprising:

arm bands for encircling the upper arms of the patient;

cross straps extending from each of the side portions to points of detachable connection to the arm bands; and a bifurcated rear anchor strap having parts connected to the cross straps and a main trunk connected to the rear side of the helmet at the back of the patient's head.

11. An electrode cap comprising:

a flexible helmet;

a plurality of spaced electrode anchoring tabs positioned at least partially inside the helmet and arrayed over a major portion of the interior thereof, each of said tabs including means for removably attaching the respective tab to a pickup electrode;

a plurality of brain wave pickup electrodes movably located within the interior of the helmet, and each including means to selectively engage said attaching means of a selected one of said anchoring tabs at variable positions thereon, each of said pickup electrodes including:

an annular mounting plate having an opening through the center thereof;

a rigid annular metallic electrode contact element positioned against one side of said annular mounting plate and having an opening through the center thereof aligned with the opening through the center of said annular mounting plate, said annular metallic contact element concentrically bonded to said annular mounting plate;

an annular cellular pad on the opposite side of said mounting plate from said rigid electrode contact element, said cellular pad defining a central opening therethrough aligned with the central opening through said annular mounting plate and through said rigid electrode contact element;

a tubular boss on the opposite side of said annular mounting plate from said annular metallic contact element, with the bore through the boss aligned with the opening through the metallic contact element and with the opening through said mounting plate, said tubular boss projecting into the cellular pad central opening, and partially through said cellular pad; and an anchor pad engaging element on the opposite side of said annular mounting plate and said rigid electrode contact element from said cellular pad, said anchor pad engaging element including means for detachably engaging the anchor pad engaging element with a selected one of said anchoring tabs.

12. An electrode cap comprising:

a flexible helmet;

a plurality of spaced electrode anchoring tabs positioned at least partially inside the helmet and arrayed over a major portion of the interior thereof, each of said tabs including means for removably attaching a pickup electrode to a respective one of the tabs;

a plurality of brain wave pickup electrodes movably located within the interior of the helmet, and each including means to selectively engage said attaching means of any selected one of said anchoring tabs at variable positions thereon;

means for electrically connecting the electrodes to a recording means; and a harness connected to said helmet for stabilizing the helmet on the head of a patient, said harness including:
  arm bands adapted for encircling the upper arms of the patient; and
  straps having first ends connected to the helmet, and having second ends connected to the arm bands.

13. An electrode cap as defined in claim 12 wherein said harness further includes
  a chest strap extending across the chest of the patient and interconnecting said arm bands; and
  a first bifurcated strap having a trunk portion detachably engaging a central portion of said chest strap, and having branch straps connected to opposite sides of said helmet.

14. An electrode cap as defined in claim 13 and further characterized as including a second bifurcated strap having a trunk portion engaged to the rear of said helmet and having branch straps connected to said chest strap.

15. An electrode cap comprising:
  a flexible helmet of see-through mesh material woven to facilitate visibility of brain wave pickup electrodes through said helmet from a vantage point outside said helmet, said helmet having a plurality of spaced openings therethrough;
  a plurality of spaced electrode anchoring tabs arranged over a major portion of the helmet, and each including:
    an annular outer disc secured to the outer side of said helmet and having a central opening therethrough aligned with one of said openings through the helmet; and
    an annular inner disc secured to the inner side of said helmet and having a central opening therethrough aligned with said one opening through the helmet and the central opening through said annular outer disc, said inner disc including a substantially flat inner side having touch adherence means thereon for engaging a portion of a pickup electrode upon contact therewith;
  a plurality of brain wave pickup electrodes movably located within the interior of the helmet, each of said electrodes including:
    a disc-shaped touch adherence anchoring element having a central opening therethrough and having an inner side and an outer side including means for engaging the inner side of said inner disc at a selected area of contact between said anchoring element and said inner disc;
    an annular mounting plate secured to the inner side of said anchoring element and having a central opening therethrough aligned with the central opening through said anchoring element;
    a tubular boss secured to one side of said mounting plate on the side thereof opposite said anchoring element and having a bore therethrough aligned with the central opening through said mounting plate;
    a resilient annular pad around said tubular boss and bearing against said mounting plate, said resilient annular pad adapted for contact with the scalp of a patient; and
    a rigid electrode contact element having a central opening therethrough aligned with the central opening through said mounting plate, and positioned between said mounting plate and said anchoring element; and
  a flexible electrically conductive lead connected to the contact element of each of said pickup electrodes and extending through said helmet from the inside to the outside thereof.

16. An electrode cap as defined in claim 15 and further characterized as including an electrode board adapter assembly, said electrode board adapter assembly including:
  a male cable connector block detachably connected to one end of each of said electricaly conductive leads;
  a female cable connector telescopingly connected with said male cable connector block;
  leads projecting from said female cable connector in correspondence to the electrically conductive leads having ends detachably connected to said male cable connector block; and
  a jack on the end of each of said last-mentioned leads.

17. An electrode cap comprising:
  a flexible helmet having a plurality of spaced openings therethrough;
  a plurality of spaced electrode anchoring tabs arranged over the major portion of the helmet, and each including:
    an annular outer disc secured to the outer side of said helmet and having a central opening therethrough aligned with one of said openings through the helmet; and
    an annular inner disc secured to the inner side of said helmet and having a central opening therethrough aligned with said one opening through the helmet and the central opening through said annular outer disc, said inner disc including means for detachably engaging a pickup electrode at any selected one of multiple locations on said inner disc;
  a plurality of brain wave pickup electrodes moveably located within the interior of the helmet, each of said electrodes including:
    a disc-shaped anchoring element having a central opening therethrough, and having an inner side and an outer side, said outer side including means for engaging the engaging means of said inner disc at said selected location;
    an annular mounting plate secured to the inner side of said anchoring element and having a central opening therethrough aligned with the central opening through said anchoring element;
    a resilient annular pad mounted on said mounting plate on the opposite side thereof from said anchoring element, said resilient annular pad adapted for contact with the scalp of a patient and having an opening therethrough aligned with the central opening through said anchoring element and the central opening through said mounting plate; and
    a rigid electrode contact element having a central opening therethrough aligned with the central opening through said mounting plate and with the central opening through said annular pad, said rigid electrode contact element located between said anchoring element and said mounting plate; and
  a flexible electrically conductive lead connected to the contact element of each of said pickup electrodes and extending through said helmet from the inside to the outside thereof.

18. An electrode cap comprising:
   a flexible head cover including spaced opposite side portions, a forehead portion and a crown flap having one end portion connected to the side portions at the back side of the head cover, and adapted to cover the crown of a patient's head by extension between said spaced side portions and detachable securement thereto;
   means for detachably securing said crown flap to said forehead portion;
   means on the inner side of said head cover to facilitate detachable securement of multiple electrodes at selectively adjustable locations on the inner side of said head cover;
   a plurality of electrodes each including means for detachably securing the respective electrode at selected locations on the inner side of said head cover to said means located thereon for detachable securement of said electrodes thereto;
   a male cable connector block;
   an electrode lead extending from each of said electrodes, through said head cover, to said male cable connector block;
   a female cable connector detachably connected to said male cable connector block,
   a plurality of electrode wires each having one end connected to said female cable connector; and
   an electrode jack connected to the other end of each of said electrode wires.

19. An electrode cap as defined in claim 18 wherein said electrode leads extend through said crown flap in extending from said electrodes through said head cover whereby detachment of said crown flap from said side portions, followed by lifting said crown flap exposes said electrodes and facilitates access to the scalp of a patient wearing the electrode cap.

20. An electrode cap as defined in claim 18 wherein said means for detachably securing the respective electrode comprises:
   a scalp side including a resilient pad; and
   a head cover side including a contact-engaging tab adapted to adhere, upon contact, to said detachable securement means.

21. An electrode cap as defined in claim 18 and further characterized as including harness means connected to the head cover and adapted to be connected to the body of the patient below the head to stabilize the head cover.

22. An electrode cap as defined in claim 18 wherein said head cover is a fabric material having a construction such that said electrodes can be visually perceived through said fabric material from the outer side of the head cover.

23. A method for sensing electrical potential generated by the brain for subsequent graphic development and depiction comprising:
   locating a plurality of discrete, disc-shaped anchoring tabs at pre-selected general locations arrayed about, and spaced outwardly from, the cranium in which the brain is located;
   choosing a critical point on each of said anchoring tabs for attachment thereto of a pickup electrode in a position between the critical point and the cranium;
   quick detachably attaching to each of said anchoring tabs at the chosen critical point thereon, a pickup electrode having a central opening therethrough and having a closed cell resilient at one side thereof, with said pad in contact with the scalp on the cranium at a predetermined location, and with said pad having a central opening therethrough aligned with the central opening through said pickup electrode;
   placing an electrically conductive material in contact with said pad and the scalp by flowing the material into the aligned central openings through said pickup electrode and said closed cell resilient pad; and
   conveying an electrical signal from each of said pickup electrodes to apparatus for graphically depicting said signals.

24. A pickup electrode useful for contacting a patient's head during electroencephalography comprising:
   a contact adhering anchoring element having a central opening therethrough, including means for engagement, upon contact, with a helmet-carried anchoring tab;
   an annular mounting plate having an opening through the center thereof;
   a tubular boss projecting from one side of the mounting plate and having a bore therethrough aligned with the central opening through the mounting plate;
   an annular metallic contact mounted between, and secured to, the anchoring element and the mounting plate and having a central opening aligned with the openings in the anchoring element, and in the mounting plate, and aligned with the bore through said tubular boss, said central opening in said metallic contact being of smaller diameter than the opening in said plate and than the diameter of the bore through said tubular boss, said metallic contact being located on the opposite side of said mounting plate from the side from which said tubular boss projects;
   a closed cell resilient pad having a central opening therethrough receiving said boss; and
   an electrical lead connected to said metallic contact.

* * * * *